United States Patent [19]

West et al.

[11] Patent Number: 5,726,344
[45] Date of Patent: Mar. 10, 1998

[54] ENANTIOMERIC ENRICHMENT OF BICYCLIC ALCOHOLS

[75] Inventors: J. Blair West, Bend, Oreg.; Keith DeVries, Old Saybrook, Conn.

[73] Assignee: Bend Research, Inc., Bend, Oreg.

[21] Appl. No.: 515,153

[22] Filed: Aug. 15, 1995

Related U.S. Application Data

[63] Continuation of Ser. No. 275,132, Jul. 13, 1994, abandoned.
[51] Int. Cl.⁶ .................................................. C07C 69/34
[52] U.S. Cl. .................................................. 560/194; 560/80
[58] Field of Search ...................................... 560/80, 194

[56] References Cited

U.S. PATENT DOCUMENTS 4,264,754  4/1981  Kageyama et al. .................... 526/283
5,270,206  12/1993  Saccomano .

OTHER PUBLICATIONS

Irwin et al., "Alcohol Dehydrogenase Catalyzed Oxidoreductions," 98 *J.A.C.S.* 8476 (1976).
Kasper et al; CA 98:143807C, 1983.
Hueckel et al.; CA66:1966, 1967.
CA98:143807 (1982).
CA66:1966 (1966).

*Primary Examiner*—Gary Geist
*Assistant Examiner*—Sreeni Padmanabhan
*Attorney, Agent, or Firm*—Chernoff, Vilhauer, McClung & Stenzel, LLP

[57] ABSTRACT

There is disclosed a two-stage enzymatically catalyzed reaction for the selective preparation of the (R)-endo-isomer of norbornenol from a mixture containing all four stereo- and regioisomers of norbornenol, as well as the synthesis of the intermediate product comprising the enantiomerically enriched mono-ester of (R)-endo-norbornenol and a diacid, and of the enantiomerically enriched saturated alcohol (R)-endo-norborneol. There is also disclosed a method for the production of (R)-endo-norborne-2-ol, by chemical reduction of either the enantiomerically enriched monoester and subsequent hydrolysis, or by hydrolysis of the enantiomerically enriched monoester and then chemical reduction.

2 Claims, No Drawings

ENANTIOMERIC ENRICHMENT OF BICYCLIC ALCOHOLS

This is a continuation of application Ser. No. 08/275,132 filed on Jul. 13, 1994 abandoned.

BACKGROUND OF THE INVENTION

Bicyclic alcohols such as norbornenol ([2.2.1]-bicyclo-hept-5-en-2-ol) and the corresponding saturated alcohol norborneol ([2.2.1]-bicyclo-heptan-2-ol) are important intermediates for the production of numerous classes of compounds including pharmaceuticals. When biologically active norbornenol derivatives are prepared that contain chiral centers, it is often highly desirable that they be in an enantiomerically enriched or pure form, so as to improve specificity and reduce side-effects. Consequently, the preparation of high optical purity bicyclic alcohols of this type is of great interest.

The resolution of racemic mixtures of alcohols through the use of enzyme-catalyzed reactions has been reported. However, to be practical, such a process must take place in two stages: a selective reaction in which a reactant selectively reacts with one enantiomer in some way; and a separation of reacted from unreacted enantiomer. It is the latter stage which often defines the practicality of a resolution process. Especially in cases where the process is practiced on a large scale, the use of an expensive, low throughput separation process (such as chromatography) or highly labor-intensive separation process (such as fractional distillation) may render the process economically unfeasible.

It has been recognized that alcohols can be resolved by enzyme-catalyzed hydrolysis of esters of the alcohol. For example, Cambou et al., in 26 *Biotechnol. Bioeng.* 1149 (1984), disclose the resolution of sec-butanol by hydrolysis of its butyric acid ester with *Candida cylindracea* lipase. However, the resolution requires fractional distillation to separate the reacted enantiomer from the unreacted enantiomer, a process that is not always practical for large-scale synthesis. The same authors also disclose the resolution of sec-butanol by esterification with butyric acid or by transesterification with the ester tributyrin. Again however, separation of the reacted from the unreacted enantiomer was accomplished by fractional distillation.

Eichberger et al., in 27 *Tetrahedron Lett.* 2844(1987), disclose the resolution of 5-norbonen-2-ol by enzyme-catalyzed hydrolysis of its acetate ester. However, chromatography must be used to separate reacted from unreacted enantiomer. Oberhauser et al., in 43 *Tetrahedron* 3931 (1987), disclose the resolution of 5-norbonen-2-ol via the enzyme-catalyzed hydrolysis of the butyrate ester. Again however, chromatography was needed to separate reacted and unreacted enantiomers. Oberhauser et al. also recognized that the endo-isomer of norbornenol exhibits different reactivity than the exo-isomer, but failed to appreciate that an enzyme-catalyzed process can be used to differentiate the exo- and endo-isomers and so provide a basis for separation of the two isomers.

The use of cyclic anhydrides in enzyme-catalyzed acylation reactions has also been disclosed. The advantage of this approach is that the resulting monoester has a free carboxylate functionality, which can be used as a "handle" to facilitate simple base aqueous extraction for separation of the reacted and unreacted enantiomers, without resorting to such techniques as chromatography or fractional distillation. Fiaud et al., in 33 *Tetrahedron Lett.* 6967(1992) disclose the resolution of (3-t-butyl)- and (3-phenylcyclobutylidene) ethanols by enzyme-catalyzed acylation using succinic anhydride. Gutman et al., in 4 *Tetrahedron Asymm.* 839 (1993) disclose the resolution of alkyl-aryl alcohols by enzymatic acylation with succinic anhydride.

Berger et al., in 1 *Tetrahedron Asymm.* 541(1990), disclose the resolution of norbornenol by enzyme-catalyzed acylation with acetic, butyric and octanoic anhydrides. However, chromatography was required to separate the reacted from the unreacted enantiomer. A process for the resolution of norbornenol using enzyme-catalyzed acylation with butyric anhydride as the acylating group is also disclosed in *Enzyme Engineering* (1992) at pages 539–551, where the separation of the reacted and unreacted enantiomers is accomplished by specialized membrane-based equipment.

SUMMARY OF THE INVENTION

Chemically synthesized preparations of norbornenol typically contain the four isomers comprising the endo- and exo-alcohols and the two enantiomeric forms of each, as shown schematically below:

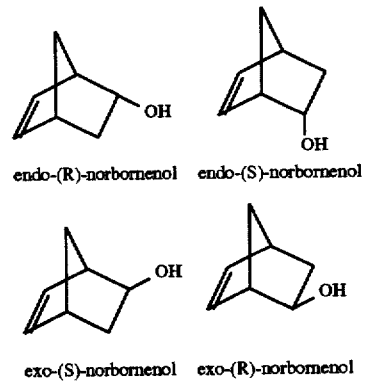

endo-(R)-norbornenol    endo-(S)-norbornenol exo-(S)-norbornenol    exo-(R)-norbornenol It has been found that (R)-endo-norbornenol can be produced in high enantiomeric and isomeric purity by first hydrolyzing (Reaction I) a mixture of the four isomers of the ester (Ester I) of the alcohol with an enzyme (Enzyme I) which is selective for the (R)-endo-isomer relative to the other isomers. The product of this hydrolysis is then reacted (Reaction II) with a cyclic anhydride in an organic solvent, using a second enzyme (Enzyme II) as a catalyst. Enzyme II is selective for the (R)-endo-isomer relative to the other isomers. Each enzyme is so chosen as to exhibit a selectivity for reacting with the (R)-endo-isomer in each reaction, such selectivity being expressed as a five-fold higher initial rate of reaction for the (R)-endo-isomer over the other three isomers. The monoester resulting from Reaction II (Ester II) can be readily isolated from the reaction mixture by extraction with basic water, or by precipitation by amine salt formation. Enantiomerically enriched (R)-endo-5-norbornen-2-ol can be released from Ester II by base hydrolysis and isolation of the resultant alcohol by extraction or distillation. It has also been found that the corresponding saturated alcohol (R)-endo-norborne-2-ol can be readily prepared in an enantiomerically enriched form by chemical reduction of either the monoester of (R)-endo-5-norbornen-2-ol or the alcohol produced from the base hydrolysis of Ester II. A preferred form of chemical reduction is by hydrogen in the presence of a catalyst such as palladium on a carbon support. The two-stage process illustrating the preparation of the enantiomerically enriched unsaturated alcohol is shown schematically below.

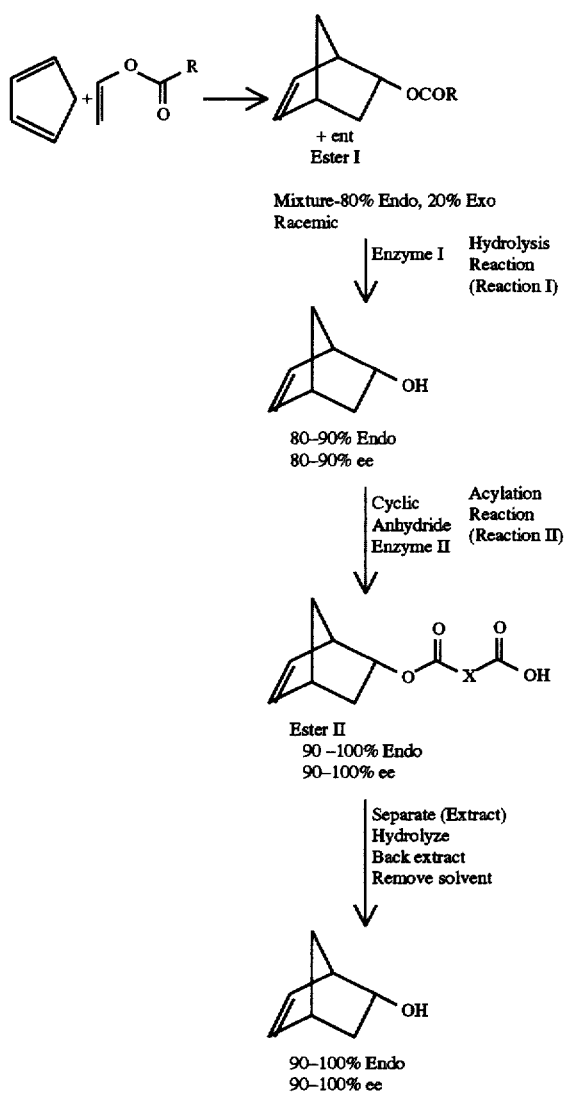

Mixture-80% Endo, 20% Exo
Racemic

The process has three distinct advantages over the prior art. First, it provides (R)-endo-norbornenol of very high enantiomeric and diastereomeric purity, even starting with material that is significantly contaminated with exo-isomers. Such contamination is often present, and it has not been recognized that enzyme-catalyzed hydrolyses/acylations can be used to purge such contaminants. For industrial-scale synthesis, this is an important consideration, as starting materials containing the exo-isomers as contaminants are often much less expensive than those not containing the contaminants.

A second advantage is that the process does not require complex or expensive separation techniques to separate the reacted from the unreacted enantiomer. Due to the large differences in solubilities of the alcohols relative to the monoester, simple liquid-liquid extraction or precipitation techniques are all that are necessary.

A third advantage is that no separation of reacted and unreacted enantiomers is necessary after the first reaction (Hydrolysis Reaction I) stage of the process. Unreacted enantiomer from the first reaction (the (S)-form of Ester I) will not react in the second reaction (Acylation Reaction II) and ultimately is purged along with the material that does not react with the cyclic anhydride.

DETAILED DESCRIPTION OF THE INVENTION

According to the present invention, there is provided a method for highly enriching a mixture of the four isomers of 5-norbonen-2-ol in the (R)-endo-isomer. The method comprises first hydrolyzing (Reaction I) a mixture of ester isomers such as that obtainable from a Diels-Alder coupling of vinyl acetate and cyclopentadiene (Ester I) with a hydrolase enzyme (Enzyme I) in a chiefly aqueous reaction medium. The hydrolytic Reaction I is preferably stopped when essentially all of the available (R)-endo-ester has been converted to the alcohol. Generally, Enzyme I is chosen so as to be selective for hydrolysis of the endo-(R) ester over the other three isomers. However, if Enzyme II has high endo over exo specificity, Enzyme I need only have selectivity toward the (R)-endo- over the (S)-endo-isomer. Preferred enzymes are esterases, proteases and lipases from mammalian, plant, bacterial, or fungal sources. Especially preferred are lipase from *Candida Antarctica* (available commercially in immobilized form as Novozyme 435 from Novo-Nordisk), and lipase from *Candida cylindracea* (commercially available as Lipase MY and OF from Meito Sangyo; as Lipase AY from Amano; and as Lipase VII from Sigma). Produced alcohol from the (R)-endo-ester, and unreacted ester (principally comprising the other three isomers, although there may be some unreacted (R)-endo-ester present) are removed from the Reaction I medium by extraction of the aqueous medium with a water-immiscible organic solvent (Solvent I). Preferred solvents are methylene chloride, ethyl ether, diisopropyl ether, and t-butyl methyl ether (TBME), with the last-mentioned being especially preferred. Produced alcohol does not need to be separated from unreacted ester since the latter does not react in the second phase Reaction II.

To the extent necessary, the solvent from Reaction I may be removed by distillation and replaced by a second solvent (Solvent II), in which Reaction II is performed. If the same solvent used in Reaction I is used in Reaction II, there is no need to change the solvent. The preferred second solvent is diisopropyl ether. Other acceptable solvents include methylene chloride, chloroform, TBME, and toluene. The (R)-endo-norbornenol is then reacted with a cyclic anhydride in the presence of another hydrolase enzyme (Enzyme II) in Reaction II. The cyclic anhydride is of the structure shown below:

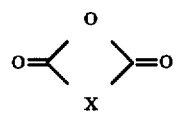

where X is a linear or branched or substituted alkylene chain of no more than 6 carbons; alkenylene, arylene, or aralkylene. Preferred cyclic anhydrides are succinic, maleic, phthalic, glutaric, and 3,3-dimethyl glutaric anhydrides. Especially preferred is succinic anhydride.

Like Enzyme I, Enzyme II is also a hydrolase enzyme such as a lipase, an esterase or a protease from mammalian, plant, bacterial or fungal sources. Especially preferred hydrolase enzymes are lipases from *Pseudomonas cepacia* and *Pseudomonas sp.* (commercially available as Amano PS-30 and Amano Sam-2, respectively, from Amano Enzymes of Troy, Va.). Enzyme II is generally chosen so as to selectively catalyze the reaction of the cyclic anhydride with the (R)-endo-alcohol over the other three alcohol isomers. If the first enzyme has high selectivity towards the endo- over exo-isomers, Enzyme II need only have selectivity towards the (R)-endo versus the (S)-endo isomers. Similarly, if Enzyme I has high selectivity toward the (R) over (S) isomers, Enzyme II need only be selective towards the endo over exo isomers. The combination of Enzyme I and Enzyme II must have an aggregate selectivity toward the (R)-endo-isomer over each of the three isomers. Enzyme II is preferably immobilized onto a solid support by absorption or by covalent bonding. Immobilization may be accomplished by preparing a slurry of the solid support in an aqueous solution of enzyme and buffer salts, removing the bulk of the water by evaporation, followed by removal of residual water by vacuum evaporation. Suitable solid supports include bleached or unbleached or calcined diatomaceous earth, polydextran, polyacrylic acid ester, silica gel, and porous glass beads. Preferred commercially available forms of diatomaceous earth are those made and sold by Johns Manville of Denver, Colo., and include Celite 577 and Celite 649. The preferred amount of enzyme loaded on the solid support is 10 wt %. Upon completion of Reaction II, Enzyme II, along with its solid support, may be removed from the reaction mixture simply by filtration.

The resulting monoester of (R)-endo-norbornenol and the diacid (Ester II) from Reaction II has intrinsic utility as an intermediate since it is in a relatively enantiomerically pure form and may readily be separated as and converted to the (R)-endo-isomer of norbornenol, which in turn may be converted by chemical reduction to the enantiomerically enriched corresponding saturated alcohol (R)-endo-norborneol, which also has intrinsic utility as an intermediate in the manufacture of pharmaceuticals. Ester II is separated from the reaction mixture and from the (S)-alcohol, (S)-ester and exo-alcohols and esters (from Reaction I) by extracting the same with basic water; the extraction is selective to Ester II, and unreacted alcohols and any Ester I left from Reaction I will remain in the organic phase. Ester II may be hydrolyzed to release the unsaturated alcohol, chemically reduced to form the saturated alcohol form of Ester II, or may be precipitated from solution by amine salt formation such as by the addition of dicyclohexylamine, and the freed (R)-endo-norbornenol can be back-extracted into a water-immiscible organic solvent.

EXAMPLE 1

Deacetylation Reaction

Two hundred and fifty grams of racemic 5-norbornen-2-yl acetate (Ester I) containing 21% exo-isomers was suspended in 750 g of water in a 2 L flask fitted with a stirring mechanism. One hundred grams of a supported lipase derived from *Candida Antarctica* (Enzyme I), commercially available as Novozyme 435, was added to the flask, pH was maintained at 7 by the addition of 1.0M NaOH, and the mixture was stirred for three hours to permit Reaction I to proceed to approximately 50% conversion, causing the hydrolysis of approximately 50% of Ester I to 5-norbornen-2-ol, based upon the amount of base added. Reuse of the same Enzyme I produced nearly identical rates of reaction, suggesting that enzyme lifetime should be at least several cycles. The reaction mixture was extracted with the solvent TBME (Solvent I) several times, the solvent was removed by distillation, and the residue was taken up in anhydrous diisopropyl ether. Gas chromatograph analysis of the extracted residue showed that its composition was 40 to 50% norbornenol, 40 to 45% acetate ester and 3 to 5% TBME. The norbornenol was 88 to 92% enantiomeric excess (ee), and the exo-isomer content had dropped from 21% to 5 to 10%.

Enzyme II Preparation

A lipase derived from *Pseudomonas cepacia* (Amano PS-30-1.25 g) was added to 25 mL of 0.1M sodium phosphate buffer (pH 7) in a crystallizing dish. The resulting turbid solution was stirred for a few moments, then 5 g of diatomaceous earth (Celite 577) was added and stirred to make a homogeneous suspension. The suspension, comprising supported Enzyme II, was allowed to air dry overnight, was collected, and was further dried under vacuum for 24 hours.

Monoesterification by Cyclic Anhydride

Using 75 g of the extracted residue from the deacetylation reaction detailed above, Enzyme II and succinic anhydride were mixed therewith to perform Reaction II. The (R)-norbornenol concentration was diluted to 600 mM with diisopropyl ether. The final Enzyme II catalyst concentration was 20 g/L (80 g/L catalyst). The reaction was stirred and succinic anhydride was added in four aliquots to a total of 1.0 equivalent based on the amount of racemic norbornenol. In approximately 10 hours, the reaction to form the monoester of (R)-endo-5-norbornen-2-ol and the diacid succinic anhydride (Ester II) proceeded to about 85% completion, based upon the total amount of racemic norbornenol. Over the next 10 hours, the reaction only proceeded an additional 3%. Addition of more succinic anhydride did not increase the reaction rate or increase the extent of conversion. The reaction was terminated by filtering off the enzyme.

Work-Up of Alcohol

Solvent from Reaction II was extracted with 10% sodium carbonate, resulting in a carbonate solution of Ester II. This solution was then back-extracted several times with TBME to remove unreacted alcohol. One equivalent of base was added to the carbonate solution to hydrolyze Ester II and, after four hours, the hydrolyzed norbornenol was extracted with TBME. Removal of the solvent yielded 18.8 g of (R)-endo-norbornen-2-ol, amounting to 50% of theoretical yield; chiral gas chromatographic analysis indicated its enantiomeric excess to be greater than 99%, with exo-content of less than 1%.

EXAMPLE 2

Example 1 was substantially repeated except lipase MY (Meito Sangyo) was used as Enzyme I. Liberated norbornenol was found to be 70% ee in the (R)-form, and to have 3% exo-isomer. The two-stage process yielded 16 g of (R)-endo-norbornenol with 98% ee containing less than 2% exo-isomer.

EXAMPLE 3

Example 1 was substantially repeated, except lipase OF (Meito Sangyo) was used as Enzyme I. Liberated norbornenol was found to be 72% ee in the (R)-form, and to have 5% exo-isomer. The two-stage process yielded 15 g of (R)-endo-norbornenol with 98% ee containing less than 2% exo-isomer.

EXAMPLE 4

Example 1 was substantially repeated, except glutaric anhydride was used in Reaction II. Reaction II reached 90% completion in four days and provided (R)-endo-norbornenol in 97% ee with less than 2% exo-isomer.

EXAMPLE 5

Example 1 was substantially repeated, except the lipase Amano Sam-II was used as Enzyme II. Reaction II reached 85% conversion in 20 hours, and provided (R)-endo-norbornenol with 99% ee having less than 1% exo-isomer.

EXAMPLE 6

The mono-ester produced in Example 1 was dissolved in ethanol and subjected to chemical reduction by hydrogen, in the presence of palladium on carbon, producing the succinate monoester of (R)-endo-norborne-2-ol in a 95% yield.

EXAMPLE 7

The alcohol (R)-endo-5-norbornen-2-ol) produced in Example 1 was dissolved in methanol and subjected to chemical reduction as in Example 6, producing (R)-endo-norborne-2-ol, in a 95% yield.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. The enantiomerically enriched mono-ester of (R)-endo-5-norbornen-2-ol and a diacid, the mono-ester having the structure

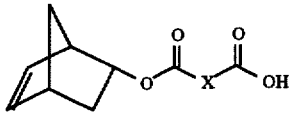

wherein X is selected from the group consisting of linear or branched or substituted alkylene containing no more than 6 carbon atoms; alkenylene; arylene; and aralkylene.

2. The enantiomerically enriched mono-ester of (R)-endo-norborne-2-ol of the structure

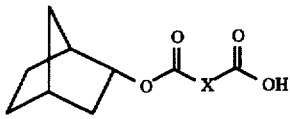

wherein X is selected from the group consisting of linear or branched or substituted alkylene containing no more than 6 carbon atoms; and alkenylene.

* * * * *

UNITED STATES PATENT AND TRADEMARK OFFICE
CERTIFICATE OF CORRECTION

PATENT NO. : 5,726,344
DATED : March 10, 1998
INVENTOR(S) : West and DeVries

It is certified that error appears in the above-identified patent and that said Letters Patent is hereby corrected as shown below:

Col. 7, line 18: Delete parenthesis after "ol" in "(R)-endo-5-norbornen-2-ol)"

Signed and Sealed this

Seventeenth Day of April, 2001

*Attest:*

NICHOLAS P. GODICI

*Attesting Officer*     *Acting Director of the United States Patent and Trademark Office*